United States Patent
Ni et al.

(10) Patent No.: US 11,191,751 B1
(45) Date of Patent: Dec. 7, 2021

(54) TOPICAL OPHTHALMOLOGICAL ATROPINE FREE BASE COMPOSITIONS

(71) Applicant: ADS THERAPEUTICS LLC, Irvine, CA (US)

(72) Inventors: Jinsong Ni, Irvine, CA (US); Rong Yang, Irvine, CA (US)

(73) Assignee: ADS THERAPEUTICS LLC, Irvine, CA (US)

( * ) Notice: Subject to any disclaimer, the term of this patent is extended or adjusted under 35 U.S.C. 154(b) by 0 days.

(21) Appl. No.: 17/317,551

(22) Filed: May 11, 2021

Related U.S. Application Data

(60) Provisional application No. 63/089,263, filed on Oct. 8, 2020.

(51) Int. Cl.
| | | |
|---|---|---|
| A61K 31/439 | (2006.01) | |
| A61K 47/06 | (2006.01) | |
| A61P 27/10 | (2006.01) | |
| A61K 9/00 | (2006.01) | |

(52) U.S. Cl.
CPC .......... *A61K 31/439* (2013.01); *A61K 9/0048* (2013.01); *A61K 47/06* (2013.01); *A61P 27/10* (2018.01)

(58) Field of Classification Search
CPC .... A61K 31/439; A61K 47/06; A61K 9/0048; A61P 27/10
See application file for complete search history.

(56) References Cited

PUBLICATIONS

Arumugama et al., Muscarinic Antagonist Control of Myopia: Evidence for M4 and M1 Receptor-Based Pathways in the Inhibition of Experimentally-Induced Axial Myopia in the Tree Shrew, Investigative Ophthalmology and Visual Science, vol. 53, No. 9. (Year: 2012).*

Carr et al, Myopia-Inhibiting Concentration of Muscarinic Receptor Antagonists Block Activation of Alpha2A-Adrenoreceptors In Vitro, Investigatie Ophthalmology and Visual Science, vol. 59, No. 7. (Year: 2018).*

* cited by examiner

*Primary Examiner* — Carlos A Azpuru
(74) *Attorney, Agent, or Firm* — SZDC Law P.C.

(57) ABSTRACT

A topical ophthalmological composition includes a muscarinic receptor antagonist as an active pharmaceutical ingredient; and a semifluorinated alkane, as a liquid vehicle. The topical ophthalmological composition treats an ocular disease.

12 Claims, 2 Drawing Sheets

TOPICAL OPHTHALMOLOGICAL ATROPINE FREE BASE COMPOSITIONS

The present application claims priority to U.S. Provisional Application No. 63/089,263, filed on Oct. 8, 2020, which is incorporated by reference for all purposes as if fully set forth herein.

FIELD OF THE INVENTION

The present invention relates to topical ophthalmological compositions of a muscarinic receptor antagonist dissolved in semifluorinated alkane as a liquid vehicle, wherein, the formulation of atropine is used for treating myopia.

BACKGROUND OF THE INVENTION

Atropine is an anti-muscarinic compound and is a competitive antagonist of muscarinic receptors. It has anti-parasympathetic functions. It is used for several indications such as anticholinergic poisoning and bradycardia. In the eye, it is traditionally used for dilating pupil. Recently, low dose of atropine is shown be able to attenuate the progression of myopia in young adults (Li 2019). For the myopia indication, atropine is approved in only a few countries as of now.

Myopia, or nearsightedness, is a condition in which people can see close objects clearly, but objects farther away appear blurred. Myopia occurs if the eyeball is too long or the cornea (the clear front cover of the eye) is too curved so that distant objects can't be focused correctly on retina. Myopia is the most common eye disorder worldwide. About 30 percent of the U.S. population has myopia. The etiology of myopia is unknown. Genetics is believed to have a role in myopia. Myopia development may be affected by how a person uses the eyes. It may occur in school-age children and progresses until about age 20. However, myopia may also develop in adults due to visual stress or health conditions such as diabetes. Myopia may increase the risk of other ocular diseases (Wu 2019).

Atropine solution (water-based) formulations have been tested in multiple clinical trials and is proven to be able to slow down the progression of myopia (Cooper 2018, Li 2019, Yam 2020). In the water-based formulation, atropine is prone to degradation at neutral pH solution once the container is open to the air, therefore, the shelf life of the product at neutral pH is often less than 1 year. Low pH of 3-6 in the formulation is used to increase the stability of atropine in solution (Berton 2020; Saito 2019). However, low pH is also known to cause irritation and discomfort in the eye.

This invention uses an organic liquid carrier to create a more stable and less irritating formulation of atropine for ocular, in particular myopia, indications.

SUMMARY OF THE INVENTION

In one embodiment, a topical ophthalmological composition includes: a muscarinic receptor antagonist as an active pharmaceutical ingredient; and a semifluorinated alkane, as a liquid vehicle. The topical ophthalmological composition treats an ocular disease.

In another embodiment, the muscarinic receptor antagonist is selected from the group consisting of atropine, pirenzepine, aclidinium bromide, benztropine, cyclopentolate, diphenhydramine, doxylamine, dimenhydrinate, dicyclomine, darifenacin, flavoxate, hydroxyzine, ipratropium, mebeverine, oxybutynin, procyclidine, scopolamine, solifenacin, tropicamide, tiotropium, trihexyphenidyl, and tolterodine.

In another embodiment, the muscarinic receptor antagonist is atropine.

In another embodiment, the atropine is in a free base form or a salt form.

In another embodiment, the concentration of the atropine in a free base form is from about 0.0001% to about 0.1% (w/w).

In another embodiment, the semifluorinated alkane is a compound of formula RFRH or of formula RFRHRF, wherein RF is a perfluorinated hydrocarbon with 15 or less carbon atoms, and wherein RH is a non-fluorinated hydrocarbon with 15 or less carbon atoms.

In another embodiment, the semifluorinated alkane is selected from F4H5, F4H6, F6H4, F6H6, F6H8 and F6H10.

In another embodiment, the semifluorinated alkane is F6H8 (perfluorohexyloctane).

In another embodiment, the topical ophthalmological composition further includes an organic cosolvent selected from the group consisting of phenylethyl alcohol, ethanol, isopropanol, glycerol, propylene glycol, and polyethylene glycol.

In another embodiment, the organic cosolvent is ethanol or phenylethyl alcohol.

In another embodiment, the concentration of ethanol is about 1% (w/w) or less, for example, 0.001% to 1% (w/w); or the concentration of phenylethyl alcohol is about 1% (w/w) or less, for example, 0.001% to 1% (w/w).

In another embodiment, the topical ophthalmological composition is a non-aqueous solution, a suspension, or an emulsion.

In another embodiment, the atropine in the topical ophthalmological composition is chemically stable for at least 0.5 year, for at least 1 year, or for at least 2 years.

In another embodiment, the topical ophthalmological composition is adapted for topically administering as eye drops to an eye of a patient.

In another embodiment, the topical ophthalmological composition causes minimal irritation in the eye.

In another embodiment, the ocular disease is myopia.

In another embodiment, the topical ophthalmological composition slows a myopia progression.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
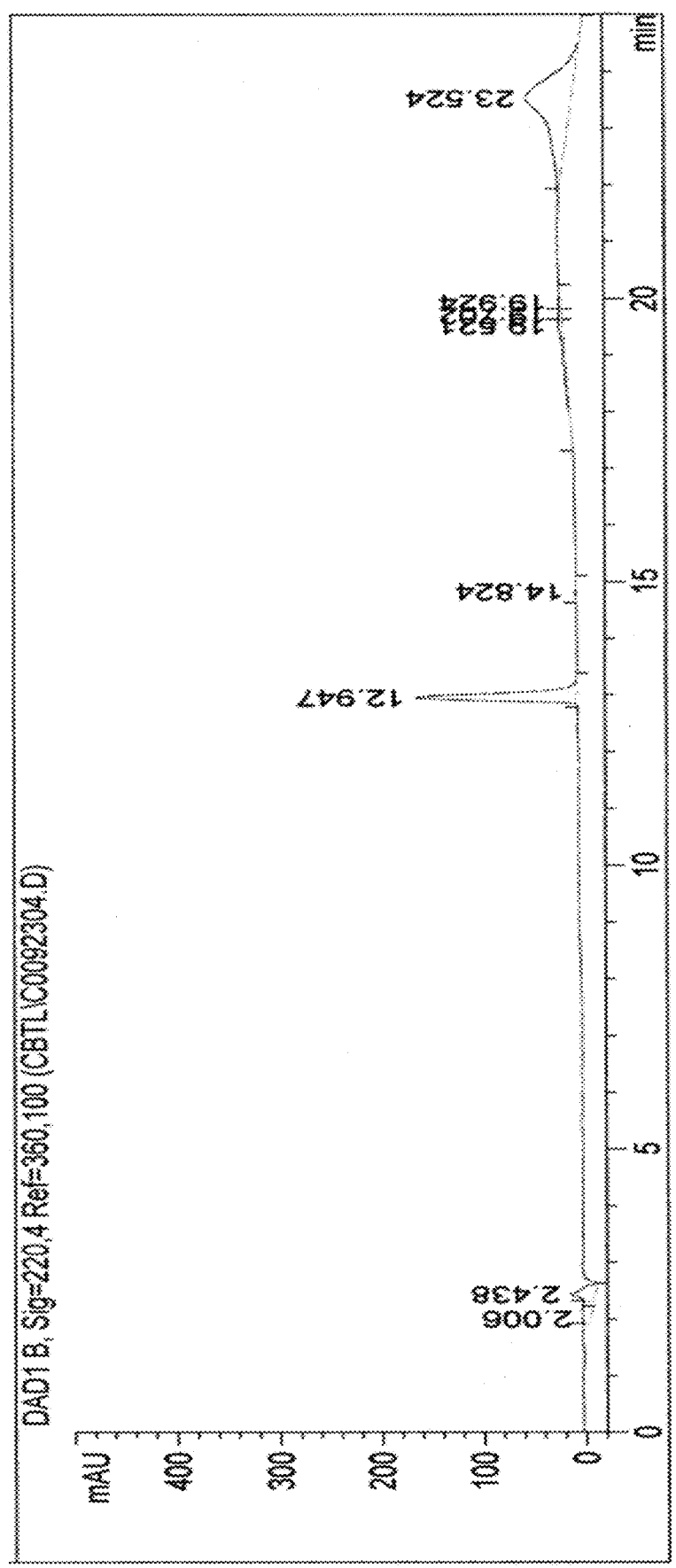
FIG. 1 shows the chromatogram of Atropine (tR: 12.947) standard solution.

Reference will now be made in detail to embodiments of the present invention, example of which is illustrated in the accompanying drawings.

A muscarinic receptor antagonist is an anticholinergic agent that blocks the activities of a muscarinic acetylcholine receptor. The muscarinic receptor antagonist may be atropine, pirenzepine, aclidinium bromide, benztropine, cyclopentolate, diphenhydramine, doxylamine, dimenhydrinate, dicyclomine, darifenacin, flavoxate, hydroxyzine, ipratropium, mebeverine, oxybutynin, procyclidine, scopolamine, solifenacin, tropicamide, tiotropium, trihexyphenidyl, or tolterodine. Preferably, the muscarinic receptor antagonist is atropine or pirenzepine. More preferably, the muscarinic receptor antagonist is atropine.

Atropine solution (water) formulations had been previously proven effective in treating myopia, specially reducing myopia progression. The solution formulation had two drawbacks. The first is that once the container opens to air, the atropine at neutral pH in the solution is prone to degradation, therefore, the shelf life of the product at neutral pH is often less than 1 year. Furthermore, this instability of the atropine in the solution requires that the formulation is used within about a month. The second shortcoming is that the low pH, such as in the pH range of 3.5 to 6.0, used to reduce atropine degradation to increase product shelf life, can cause irritation or discomfort to the human eye as reported of adverse events in the patients.

This disclosure provides compositions using a semifluorinated alkane, in particular F6H8 (perfluorohexyloctane), as the liquid vehicle to dissolve atropine to eliminate the two shortcomings of the solution formulation. F6H8 is an amphiphilic liquid with two mutually immiscible moieties (hydrocarbon segment as RH and perfluorinated segment as RF) bound covalently. Other related analogies used in the compositions of the present inventions may be F4H5 (perfluorobutylpentane), F4H6 (perfluorobutylhexane), F6H4 (perfluorohexylbutane), F6H6 (perfluorohexylhexane), and F6H10 (perfluorohexyldecane).

The structure of F6H8 is shown below.

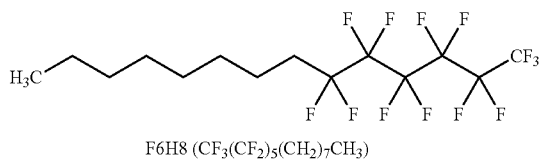

F6H8 (CF$_3$(CF$_2$)$_5$(CH$_2$)$_7$CH$_3$)

In some embodiments, the disclosure is based on the studies described in the examples that show atropine can be dissolve in F6H8 at sufficient concentration to have biological efficacy. The formulation of atropine in F6H8 is stable for prolonged times at room temperature and can be made into a product with sufficient self-life for regulatory approval. This formulation is not irritating in the eye in animal model studies when dosed at a concentration higher than what is needed for some indications.

EXAMPLES

Example 1: Dissolution of Atropine in F6H8

Methods: Formulations of atropine free base were investigated according to the following procedure:

1. Dissolving Atropine

Added more than 4 mg of atropine powder in 4 mL of F6H8 or F6H8 with 0.1% ethanol, yielding about 1 mg/mL. Stirred the formulation for 2 days.

2. Preparing HPLC Samples

Centrifuged the formulations above and filtered the supernatants through 0.45 micron filters without further dilution. One sample was prepared from each solvent for HPLC analysis.

3. Analyzing the HPLC Samples

The samples were analyzed using a RP-HPLC method with an Agilent Eclipse Plus C18 HPLC column (150 mm×2.1 mm I.D.) connected with a guard column (12.5 mm×2.1 mm I.D.) and a gradient elution from 100% water to 100% acetonitrile at a flow rate of 0.2 ml/min. The chromatograms were monitored at UV at 220 nm. The atropine peak is at retention time 12.947 as shown in the chromatograph in FIG. 1.

Results

The solubility of atropine was determined to be 129 μg/ml (0.0129% w/w) in F6H8 alone. When 0.1% ethanol was added, the solubility was 171.5 μg/ml (0.0173% w/w). In this particular study, the free base form of atropine was used, while the mono sulfate salt was previously used in the solution formulation approved for myopia usage. The 1\4W of the free base is 83% equivalent to the mono sulfate salt form of atropine solution formulation. The 0.01% atropine mono sulfate salt solution was previously shown effective for myopia treatment in the clinic and was approved in several countries. This 0.01% atropine salt concentration was equivalent to 0.0083% of the free base concentration. Since the maximum atropine free base that we observed in F6H8 was 0.0129%, we concluded that the F6H8 formulation can deliver sufficient amount of atropine for the treatment of myopia. The 0.0129% concentration we observed was about 55% higher than the 0.0083% needed for efficacy. In addition, we observed that the concentration of atropine can be increased further by adding ethanol to the formulation. The addition of just 0.1% ethanol increased the solubility by 33%. Higher levels of ethanol would likely further increase the solubility of atropine in F6H8. The concentrations of atropine in the F6H8 formulations are show in Table 1.

TABLE 1

Concentrations of Atropine in F6H8 formulations

| Sample Descriptions | Atropine in F6H8 | Atropine in F6H8 with 0.1% (v/v) Ethanol |
|---|---|---|
| Solubility (concentrations) | 129.0 μg/mL | 171.5 μg/mL |

Example 2: The Atropine F6H8 Formulation is Stable Over Time

Methods

Atropine is dissolved in F6H8 as described in Example 1. The level of atropine is measure by the HPLC method at 25° C. at 1, 3, 6, 9 and 12 months. The atropine in the formulation is defined as stable if the level is maintained between 90-110% of the original level.

Results

During the study period, atropine is stable as shown in Table 2 below.

TABLE 2

Atropine stability in F6H8 formulation

| Time point (month) | 1 | 3 | 6 | 9 | 12 |
|---|---|---|---|---|---|
| Remaining 90-110% of time zero (yes/no) | yes | yes | yes | yes | yes |

Example 3: The Atropine F6H8 Formulation is Tolerable in a Rabbit Study

Methods

The atropine F6H8 formulation is evaluated in rabbits for ocular tolerability. The study design and assessments are shown in Tables 3 and 4.

TABLE 3

Experiment Design

| Group | Number of Animals & Sex | Right Eye | Left Eye | Dose Frequency |
|---|---|---|---|---|
| 3 | 3F | Vehicle | 0.01% atropine | Four Times per day, 4 hrs apart |

TABLE 4

Study Assessments

| Parameters | Descriptions |
|---|---|
| Viability | Twice daily |
| Clinical Observation | Once during the predose and once daily during the dosing phase after the last daily dose. |
| Body weight | Once during the predose, and on Day 1, Day 7 and Day 14 |
| Food consumption | Once daily during predose and dosing phase |
| Ocular Discomfort observation | Twice (on different days) during the predose phase, daily during the dosing phase after the last daily dose. Both eyes will be grossly examined and graded using a modified Hackett-McDonald grading scale by technical staff |
| Ocular Irritation Observation (Modified Hackette McDonald) | Twice (on different days) during the predose phase, daily during the dosing phase after the third daily dose. Both eyes will be grossly examined and graded using a modified Hackett-McDonald grading scale by technical staff |
| Cornea Examination | Once predose phase and once after the last daily dose on Day 1 and Day 14. Both eyes will be examined for corneal opacity and % of corneal opacity using slit lamp and will be taken photos. |

Results and Conclusions

The atropine formulation is well tolerated in rabbits with no significant irritation and discomfort issues.

Example 4: Stability of Atropine in F6H8

0.01% atropine was dissolved in F6H8 and 0.25% phenylethyl alcohol. The stability of the atropine formulation over time was accessed at 25° C. and 40° C. At selected time points, atropine was extracted with acetonitrile twice and quantitated by HPLC as describe in Example 1. Table 5 below shows that atropine levels remained stable at Days 32 and 84 without significant change from the baseline at Day 0. The results were similar at both room temperature and accelerated temperature. The stability at accelerated temperature indicated that the formulation can be potentially stored at room temperature for months or years without significant loss of atropine. This example, disclosed for the first time, demonstrated that the atropine formulation in the invention was stable for prolonged storage at room temperature.

TABLE 5

Stability of atropine in F6H8 and 0.25% phenylethyl alcohol

| | 25° C. | | 40° C. | |
|---|---|---|---|---|
| Time (days) | Concentration (µg/mL) | % of time 0 | Concentration (µg/mL) | % of time 0 |
| 0 | 99.2 | | 99.2 | |
| 32 | 94.0 | 94.8% | 94.5 | 95.3% |
| 84 | 110.8 | 111.7% | 114.3 | 115.2% |

Example 5: In Vivo Ocular Tolerability in Rabbits

Study Design:

Three (3) female Dutch belted rabbits were given 40 µL of Control Article (0.01% atropine sulfate monohydrate in normal saline) to the right eyes and 40 µL of 0.012% atropine free base in 0.25% phenylethyl alcohol (PEA) in F6H8 to the left eyes, 1 drop/eye, twice per day, 12 hrs apart for 14 consecutive days. Ocular discomfort observation and ocular irritation observation were performed for all animals at predose (twice, on different days) and daily during the dosing phase after the last daily dose. Cornea examination were performed for all animals at predose (once) phase and once after the last daily dose on Day 1 and Day 14. The first dosing day were designated as Day 1.

The ocular irritation scores on Day 14 were shown Table 6 below. Other time points had similar or better results.

TABLE 6

Day 14

| Animal ID | Subject | Cornea Opacity intensity | | Cornea Opacity area | | Iris | | Conjunctiva Congestion | | Conjunctiva Swelling | | Conjunctiva Discharge | |
|---|---|---|---|---|---|---|---|---|---|---|---|---|---|
| | | OD | OS | OD | OS | OD | OS | OD | OS | OD | OS | OD | OS |
| C0866 | 1501 | 0 | 0 | 0 | 0 | 0 | 0 | 0 | 0 | 1 | 1 | 0 | 0 |
| C0863 | 1502 | 0 | 0 | 0 | 0 | 0 | 0 | 0 | 0 | 1 | 1 | 0 | 0 |
| C0867 | 1503 | 0 | 0 | 0 | 0 | 0 | 0 | 0 | 0 | 1 | 1 | 0 | 0 |

McDonald-Shadduck scoring (categories with positive scores) was shown in Table 7 below.

TABLE 7

| Animal ID | Subject | Conjuctiva | | | | Aqueous | | | | Cornea | | | | | | |
| | | Congestion | | Discharge | | Flare | | Iris | | Cloudiness | | Cloudiness Area | | Pannus | | Fluorescein |
| | | OD | OS | OD | OS | OD | OS | OD | OS | OD | OS | OD | OS | OD OS | | OD | OS |
|---|---|---|---|---|---|---|---|---|---|---|---|---|---|---|---|---|---|
| Day 1 | | | | | | | | | | | | | | | | | |
| C0866 | 1501 | 0 | 0 | 0 | 0 | 1 | 0 | 0 | 0 | 0 | 0 | 0 | 0 | 0 | 0 | 0 | 1 | 0 |
| C0863 | 1502 | 0 | 0 | 0 | 0 | 0 | 0 | 0 | 0 | 0 | 0 | 0 | 0 | 0 | 0 | 0 | 0 | 1 |
| C0867 | 1503 | 0 | 0 | 1 | 1 | 0 | 0 | 0 | 0 | 0 | 0 | 0 | 0 | 0 | 0 | 0 | 0 | 0 |
| Day 14 | | | | | | | | | | | | | | | | | |
| C0866 | 1501 | 0 | 0 | 1 | 1 | 1 | 1 | 0 | 0 | 0 | 0 | 0 | 0 | 0 | 0 | 0 | 0 | 0 |
| C0863 | 1502 | 0 | 0 | 1 | 1 | 1 | 1 | 0 | 0 | 0 | 0 | 0 | 0 | 0 | 0 | 0 | 0 | 1 |
| C0867 | 1503 | 0 | 0 | 1 | 1 | 1 | 0 | 0 | 0 | 0 | 0 | 0 | 0 | 0 | 0 | 0 | 1 | 0 |

Conclusion: The atropine formulation was well tolerated in all animals. No significant ocular irritation or ophthalmic findings were observed in any animals. There were no test article-related effects on body weights and food consumption during the studies in both species. There were no other test article-related ophthalmologic findings during the scheduled examinations for all animals. This Example demonstrated the safety of the claimed novel formulation of atropine for ocular use.

Example 6: In Vivo Ocular Tolerability in Dogs

Study Design

Three (3) male Beagle dogs were given 40 μL of Control Article (0.01% atropine sulfate monohydrate in normal saline) to the right eyes and 40 μL of 0.012% atropine free base in 0.25% phenylethyl alcohol (PEA) in F6H8 to the left eyes, 1 drop/eye, twice per day, 12 hrs apart for 14 consecutive days. Ocular discomfort observation and ocular irritation observation were performed for all animals at predose (twice, on different days) and daily during the dosing phase after the last daily dose. Cornea examination were performed for all animals at predose (once) phase and once after the last daily dose on Day 1 and Day 14. The first dosing day was designated as Day 1.

The ocular irritation scores on Day 14 were shown in Table 8 below. Other time points had similar or better results.

TABLE 8

Day 14

| Animal ID | Subject | Cornea | | | | | | Conjunctiva | | | | | |
| | | Opacity intensity | | Opacity area | | Iris | | Congestion | | Swelling | | Discharge | |
| | | OD | OS | OD | OS | OD | OS | OD | OS | OD | OS | OD | OS |
|---|---|---|---|---|---|---|---|---|---|---|---|---|---|
| 8525538 | 1001 | 0 | 0 | 0 | 0 | 0 | 0 | 1 | 1 | 0 | 0 | 0 | 0 |
| 8370950 | 1002 | 0 | 0 | 0 | 0 | 0 | 0 | 0 | 0 | 0 | 0 | 0 | 0 |
| 8473172 | 1003 | 0 | 0 | 0 | 0 | 0 | 0 | 1 | 1 | 0 | 0 | 0 | 0 |

McDonald-Shadduck scoring (categories with positive scores) was shown in Table 9 below.

TABLE 9

| Animal ID | Subject | Conjuctiva | | | | Aqueous | | | | Cornea | | | | | | |
| | | Congestion | | Discharge | | Flare | | Iris | | Cloudiness | | Cloudiness Area | | Pannus | | Fluorescein |
| | | OD | OS | OD | OS | OD | OS | OD | OS | OD | OS | OD | OS | OD OS | | OD | OS |
|---|---|---|---|---|---|---|---|---|---|---|---|---|---|---|---|---|---|
| Day 1 | | | | | | | | | | | | | | | | | |
| 8525538 | 1001 | 0 | 0 | 0 | 0 | 1 | 1 | 0 | 0 | 0 | 0 | 0 | 0 | 0 | 0 | 0 | 0 | 1 |
| 8370950 | 1002 | 0 | 0 | 0 | 0 | 0 | 1 | 0 | 0 | 0 | 0 | 0 | 0 | 0 | 0 | 0 | 0 | 1 |
| 8473172 | 1003 | 0 | 0 | 0 | 0 | 0 | 0 | 0 | 0 | 0 | 0 | 0 | 0 | 0 | 0 | 0 | 0 | 0 |

TABLE 9-continued

| Animal | | Conjuctiva | | | | Aqueous | | | | Cornea | | | | | | | |
| --- | --- | --- | --- | --- | --- | --- | --- | --- | --- | --- | --- | --- | --- | --- | --- | --- | --- |
| | | Congestion | | Discharge | | Flare | | Iris | | Cloudiness | | Cloudiness Area | | Pannus | | Fluorescein | |
| ID | Subject | OD | OS | OD | OS | OD | OS | OD | OS | OD | OS | OD | OS | OD | OS | OD | OS |
| Day 14 | | | | | | | | | | | | | | | | | |
| 8525538 | 1001 | 1 | 1 | 0 | 0 | 0 | 0 | 0 | 0 | 0 | 0 | 0 | 0 | 0 | 0 | 0 | 0 |
| 8370950 | 1002 | 0 | 0 | 0 | 0 | 0 | 0 | 0 | 0 | 0 | 0 | 0 | 0 | 0 | 0 | 0 | 0 |
| 8473172 | 1003 | 1 | 1 | 0 | 0 | 0 | 0 | 0 | 0 | 0 | 0 | 0 | 0 | 0 | 0 | 0 | 0 |

Conclusion: The atropine formulation was well tolerated in all animals. No significant ocular irritation or ophthalmic findings were observed in any animals. There were no test article-related effects on body weights and food consumption during the studies in both species. There were no other test article-related ophthalmologic findings during the scheduled examinations for all animals. This Example demonstrated the safety of the claimed novel formulation of atropine for ocular use.

Example 7: In Vivo Pharmacological Potency in a Rabbit Model

The pharmacological potency of the atropine formulation in F6H8 and 0.25% phenylethyl alcohol was tested in a rabbit model. The potency was measured as pupil dilation in normal naïve rabbits. Three concentrations of the F6H8 formulation of atropine (0.012%, 0.01%, 0.08%) were compared to that of an aqueous formulation of 0.01% atropine which was known to have good pupil dilation effects. One drop of each formulation was dosed into the eye and pupil size was measured during the following 8 hours.

Study Design

Fifteen (15) female Dutch belted rabbits were assigned to five groups, which included 3 animals/group. Three (3) female Dutch belted rabbits were randomly assigned to each group by Provantis or Excel based on body weight. The dosing of animals was performed in 2 phases, Phase 1 and Phase 2.

In phase 1, each animal was given 40 μL of testing article (see Table 10 below) to both eyes. First day of dosing was designated as Day 1. The pupil size of both eyes of all animals were measured at baseline (30 minutes before dosing), 0.5 h, 1 h, 2 h, 3 h, 4 h, 6 h, 8 h after dosing on day 1. The pupil size measurement data were analyzed for efficacy to determine which doses of atropine free base in Vehicle was equivalent to the dose of the control group of 0.01% atropine sulfate monohydrate in normal saline. Animals were allowed 2 days for wash-out period.

In phase 2, each animal was given 40 μL of testing article (see Table 11 below) to both eyes for 14 days. First day of dosing in Phase 2 was designated as Day 4. The pupil size of both eyes of all animals were measured at baseline (30 minutes before dosing), 0.5 h, 1 h, 2 h, 3 h, 4 h, 6 h, 8 h after dosing on Day 4 and Day 17.

TABLE 10

The study design of phase 1

| Group/Code Color | Animals[a] | Treatment Both eyes | Animal Number Female | Dosage & Frequency |
| --- | --- | --- | --- | --- |
| 1/White | 3 | 0.01% atropine sulfate monohydrate in normal saline | 1501-1503 | Once a day, 1 drop/eye, on Day 1 followed by 2 days wash-out period |
| 2/Green | 3 | 0.012% atropine free base in Vehicle | 2501-2503 | |
| 3/Yellow | 3 | 0.008% atropine free base in Vehicle | 3501-3503 | |
| 4/Red | 3 | 0.005% atropine free base in Vehicle | 4501-4503 | |
| 5/Cyan | 3 | Vehicle | 5501-5503 | |

Note:
[a]Replacement animals, if any, will be numbered per Testing Facility SOP and will be included in the study report.
Vehicle: 0.25% phenylethyl alcohol in 1-(perfluorohexyl)octane

TABLE 11

The study design of phase 2

| Group/Code Color | Animals[a] | Treatment Both eyes | Animal Number Female | Dosage & Frequency |
| --- | --- | --- | --- | --- |
| 1/White | 3 | 0.01% atropine sulfate monohydrate in normal saline | 1501-1503 | Once a day, 1 drop/eye, on Day 4 to Day 17. Pupil size will be measured on Day 4 and Day 17 only. |
| 2/Green | 3 | Dose to be determined after Day 1[b] | 2501-2503 | |
| 3/Yellow | 3 | Dose to be determined after Day 1[b] | 3501-3503 | |
| 4/Red | 3 | Dose to be determined after Day 1[b] | 4501-4503 | |
| 5/Cyan | 3 | Vehicle | 5501-5503 | |

Figure 2:
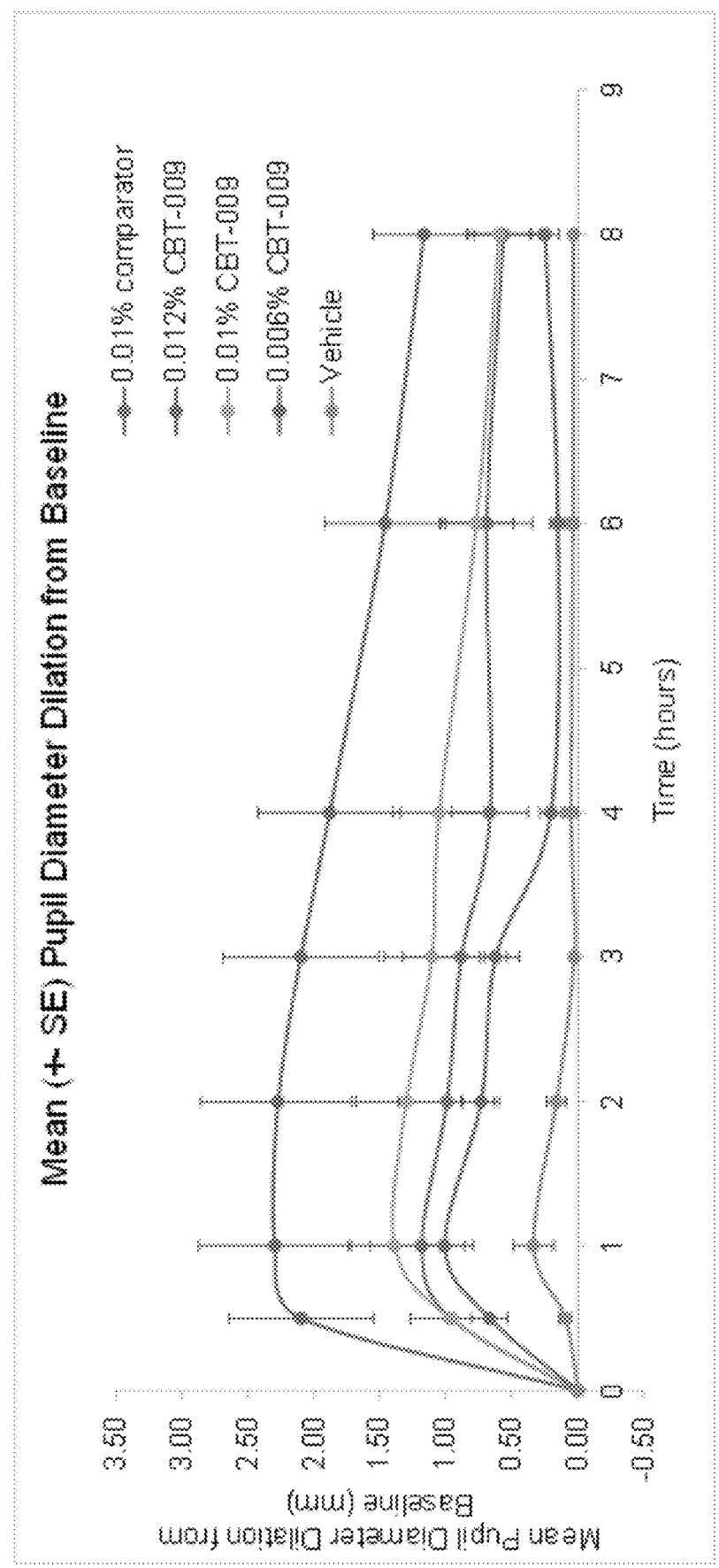
FIG. 2 shows pupil dilation effect in rabbit: CBT-009=atropine F6H8 formulation; Comparator=atropine water formulation.

Note:
[a]Replacement animals, if any, will be numbered per Testing Facility SOP and will be included in the study report.
[b]Equivalent dose is determined from Phase 1 efficacy data. The optimized concentrations of atropine free base in Vehicle that gives equivalent efficacy as 0.01% atropine sulfate monohydrate in normal saline.
Vehicle: 0.25% phenylethyl alcohol in 1-(perfluorohexyl)octane Results As shown in FIG. 2, the F6H8 formulation of atropine increased pupil size with similar potency to that of the water formulation. The 0.01% F6H8 formulation was slightly more effective than the water formulation. This observation indicated that the novel F6H8 of atropine was as effective as a proven atropine formulation and can be used for the treatment of diseases with water-based formulations. FIG. 2 showed pupil dilation effect in rabbit: CBT-009=atropine F6H8 formulation; Comparator=atropine water formulation.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

REFERENCES

Berton B, Chennell P, Yessaad M, Bouattour Y, Jouannet M, Wasiak M, Sautou V. Stability of Ophthalmic Atropine Solutions for Child Myopia Control. Pharmaceutics. 2020 Aug. 17; 12(8):E781.
Cooper J, Tkatchenko A V. A Review of Current Concepts of the Etiology and Treatment of Myopia. Eye Contact Lens. 2018 July; 44(4):231-247.
Li F F, Yam J C. Low-Concentration Atropine Eye Drops for Myopia Progression. Asia Pac J Ophthalmol (Phila). 2019 September-October; 8(5):360-365.
Saito J, Imaizumi H, Yamatani A. Physical, chemical, and microbiological stability study of diluted atropine eye drops. J Pharm Health Care Sci. 2019 Dec. 5; 5:25.
Wu P C, Chuang M N, Choi J, Chen H, Wu G, Ohno-Matsui K, Jonas J B, Cheung C M G. Update in myopia and treatment strategy of atropine use in myopia control. Eye (Lond). 2019 January; 33(1):3-13.
Yam J C, Li F F, Zhang X, Tang S M, Yip B H K, Kam K W, Ko S T, Young A L, Tham C C, Chen L J, Pang C P. Two-Year Clinical Trial of the Low-Concentration Atropine for Myopia Progression (LAMP) Study: Phase 2 Report. Ophthalmology. 2020 July; 127(7):910-919.

What is claimed is:

1. A topical ophthalmological composition comprising:
   atropine as an active pharmaceutical ingredient; and
   a semifluorinated alkane, as a liquid vehicle,
   wherein the topical ophthalmological composition treats myopia for those in need thereof,
   wherein the atropine is in a free base form, and
   wherein a concentration of the atropine in a free base form is from about 0.0083% to about 0.0129% (w/w).

2. The topical ophthalmological composition of claim 1, wherein the semifluorinated alkane is a compound of formula RFRH or of formula RFRHRF, wherein RF is a perfluorinated hydrocarbon with 15 or less carbon atoms, and wherein RH is a non-fluorinated hydrocarbon with 15 or less carbon atoms.

3. The topical ophthalmological composition of claim 2, wherein the semifluorinated alkane is selected from the group consisting of F4H5, F4H6, F6H4, F6H6, F6H8 and F6H10.

4. The topical ophthalmological composition of claim 3, wherein the semifluorinated alkane is F6H8 (perfluorohexyloctane).

5. The topical ophthalmological composition of claim 1, further comprising an organic cosolvent selected from the group consisting of phenylethyl alcohol, ethanol, isopropanol, glycerol, propylene glycol, and polyethylene glycol.

6. The topical ophthalmological composition of claim 5, wherein the organic cosolvent is ethanol or phenylethyl alcohol.

7. The topical ophthalmological composition of claim 6, wherein the concentration of ethanol is about 1% (w/w) or less; or the concentration of phenylethyl alcohol is about 1% (w/w) or less.

8. The topical ophthalmological composition of claim 1, wherein the topical ophthalmological composition is a non-aqueous solution, a suspension, or an emulsion.

9. The topical ophthalmological composition of claim 8, wherein the atropine in the topical ophthalmological composition is chemically stable for at least 0.5 year, for at least 1 year, or for at least 2 years.

10. The topical ophthalmological composition of claim 1, wherein the topical ophthalmological composition is adapted for topically administering as eye drops to an eye of a patient.

11. The topical ophthalmological composition of claim 10, wherein the topical ophthalmological composition causes minimal irritation in the eye.

12. The topical ophthalmological composition of claim 1, wherein the topical ophthalmological the composition slows a myopia progression.

* * * * *